United States Patent

Chern et al.

Patent Number: 4,929,728
Date of Patent: May 29, 1990

[54] PROCESS FOR PREPARING 3-(1H-TETRAZOL-5-YL)-4(3H)-QUINAZOLINONE

[75] Inventors: Ji-Wang Chern; Kang-Chien Liu; Chia-Yin Chen, all of Taipei, Taiwan

[73] Assignee: National Science Council, Taipei, Taiwan

[21] Appl. No.: 430,285

[22] Filed: Nov. 2, 1989

[51] Int. Cl.⁵ .................................... C07D 401/04
[52] U.S. Cl. .................................................. 544/284
[58] Field of Search ........................................ 544/284

[56] References Cited
U.S. PATENT DOCUMENTS
4,795,750  1/1989  Schlager ........................... 544/284

Primary Examiner—Mary C. Lee
Assistant Examiner—Robert C. Whittenbaugh
Attorney, Agent, or Firm—Cushman, Darby & Cushman

[57] ABSTRACT

A process for preparing 3-(1H-tetrazol-5-yl)-4(3H)-quinazolinone ammonium salts of the formula I:

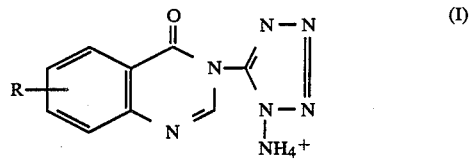

wherein:
R is hydrogen, halogen, $C_1$-$C_3$ alkyl or $C_1$-$C_3$ alkoxy, which process comprises:
reacting ethyl N-(1H-tetrazol-5-yl) formimidate in an inert solvent with substituted anthranilamide of the formula IV

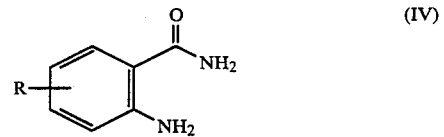

wherein R is as defined above. The process is simpler than prior processes for preparing the same compounds and thus is economically valuable.

5 Claims, No Drawings

PROCESS FOR PREPARING 3-(1H-TETRAZOL-5-YL)-4(3H)-QUINAZOLINONE

BACKGROUND OF THE INVENTION 3-(1H-tetrazol-5-yl)-4(3H)-quinazolinone derivatives of formula I:

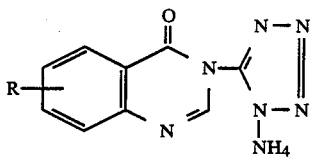

are known compounds. The free base form of the compound is known to be a highly effective antiallergic agent for oral administration. The antiallergic agent is now under clinical evaluation. U.S. Pat. No. 4,419,357 and *Journal of Medical Chemistry*, pp. 2403-1409, Vol. 29, 1986 disclosed a process for preparing the compound in free base form by reaction of o-nitrobenzoyl chloride with 5-amino-tetrazole followed by hydrogenation, cyclization and finally forming sodium salt through reaction with sodium hydroxide. The yield of the process is only about 23%. The process comprises four steps and requires hydrogenation equipment and therefore is very costly.

SUMMARY OF THE INVENTION

It is therefore an object of the present invention to provide a more efficient process for preparing 3-(1H-tetrazol-5-yl)-4(3H)-quinazolinone derivatives.

According to the present invention, there is provided a process for preparing 3-(1H-tetrazol-5-yl)-4(3H)-quinazolinone ammonium salts of the formula I:

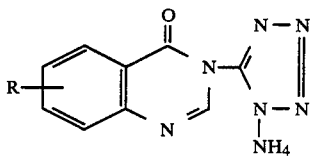

wherein:
R is hydrogen, halogen, $C_1$-$C_3$ alkyl or $C_1$-$C_3$ alkoxy, preferably hydrogen,
which process comprises:
reacting ethyl N-(1H-tetrazol-5-yl) formimidate in an inert solvent with substituted anthranilamide of the formula IV
wherein R is as define above.

DETAILED DESCRIPTION OF THE INVENTION

The individual elements of the present invention will illustrated in detail below.

Ethyl N-(1H-tetrazol-5-yl) formimidate can be prepared by reacting 5-amino-tetrazole with triethyl orthoformate. No purification is required for the intermediate product. The mole ratio of 5-amino-tetrazole to triethyl orthoformate is from 1:1 to 1:5, preferably from 1:1 to 1:3. The reaction temperature is from 60° to 150° C., preferably from 80° to 120° C. The reaction is preferably carried out in an solvent such as acetonitrile, N,N-dimethyl formamide, formamide, dioxane. The reaction time is from 1 to 12 hours, preferably from 1 to 2 hours.

The resultant ethyl N-(1H-tetrazol-5-yl) formimidate can then react directly with substituted anthranilamide (IV) to give the desired 3-(1H-tetrazol-5-yl)-4(3H)-quinazolinone ammonium salts (I). The mechanism of the reaction of the subject invention can be depicted as follows:

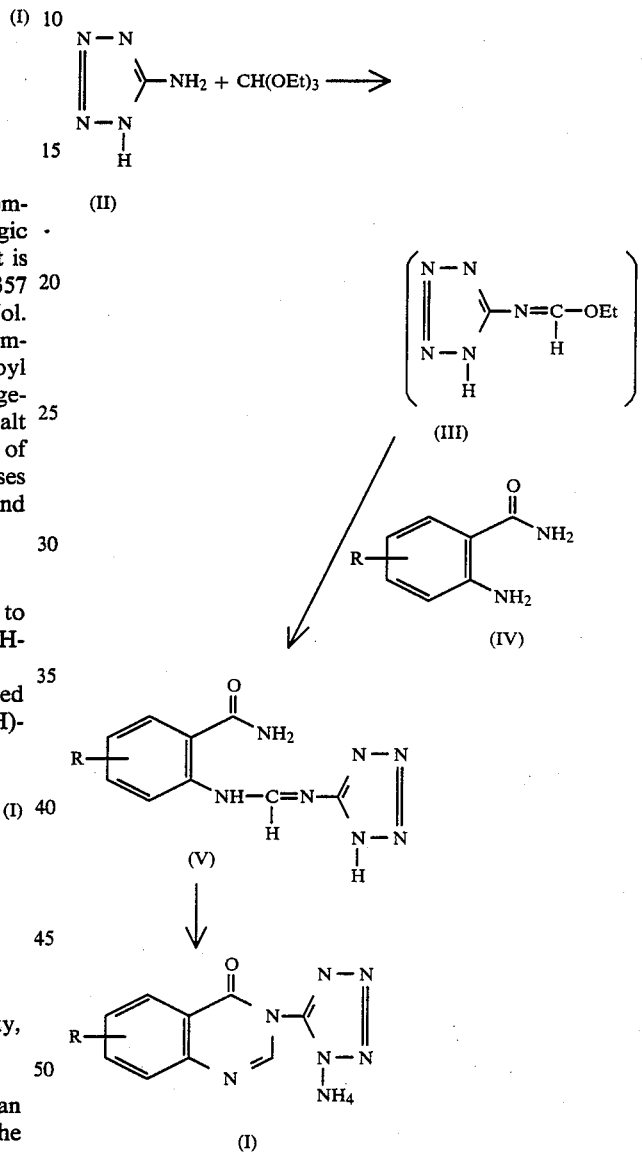

The characteristic of the present invention resides in the step that the N-(1H-tetrazol-5-yl)-$N^1$-(3-benzamino-2-yl) amidine of formula V which is the reaction intermediate of substituted anthranilamide (IV) and ethyl N-(1H-tetrazol-5-yl) formimidate will undergo cyclization reaction automatically to give the final product of 3-(1H-tetrazol-5-yl)-4(3H)-quinazolinone ammonium salts (I) by releasing the amino group. The auto-cyclization reaction does not require the addition of base or any purification and thus can be carried out in the same reaction mixture. The process is therefore greatly simplified as a one-step operation.

In the reaction for the production of the compound of formula (I), the mole ratio of ethyl N-(1H-tetrazol-5-yl)

formimidate (III) to substituted anthranilamide (IV) is about 1:1. The reaction temperature is from 50° to 150° C., preferably from 80° to 100° C. The reaction time is from about 15 to about 48 hours, preferably about 24 hours. The final product of formula (I) can be recovered from the resultant reaction mixture by conventional methods such as filtration or column chromatography.

The process of the present invention is greatly simplified as compared with conventional method. The yield is also significantly improved. Furthermore, according to the report in *Journal of Medical Chemistry*, pp. 2403–2409, Vol. 29, 1986, the sodium salt of 3-(1H-tetrazol-5-yl)-4(3H)-quinazolinone exhibits better effectiveness than the corresponding free bases. This is another aspect of the present invention.

The following examples are offered to aid in understanding of the present invention and are not to be construed as limiting the scope thereof. Unless otherwise indicated, all parts and percentages are by weight.

EXAMPLE 3-(1H-tetrazol-5-yl)-4(3H)-quinazolinone ammonium salt 5 g of 5-amino-tetrazole and 10 ml of triethyl orthoformate were dissolved in 10 ml of N,N-dimethyl formamide and heated under reflux for 1 hour. The temperature was then lowered to 80° C. and 5.64 g of o-nitrobenzoyl amine was added into the reaction mixture. The temperature was kept at 80° C. for 15 minutes and the mixture was cooled, concentrated, and then 20 ml of acetone was added. The resultant white solid was filtered and washed with a small amount of acetone. The solid was re-crystallized by ethanol and 3.27 g of the title compound, yield 34%, m.p. 225° C., was obtained.

IR (KBr): 1676 (C=O) cm$^{-1}$
MS: m/e=214 (M$^+$)
'H NMR (100 MHz, DMSO-d6): δ 8.1 (S, 1H, C=H), 7.5–8.0 (m, 4H, Ar-H), 7.1 (s, 4H, NH$_4$)

Analysis for C$_8$H$_8$N$_7$O:
Calc.: C, 46.75; H, 3.92; N, 42.40;
Found: C, 46.54; H, 3.80; N, 42.43.

We claim:
1. A process for preparing 3-(1H-tetrazol-5-yl)-4(3H)-quinazolinone ammonium salts of formula I:

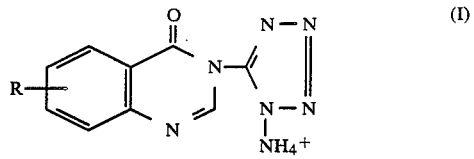

wherein:
R is hydrogen, halogen, C$_1$–C$_3$ alkyl or C$_1$–C$_3$ alkoxy,
which process comprises:
reacting ethyl N-(1H-tetrazol-5-yl) formimidate in an inert solvent with substituted anthranilamide of formula IV

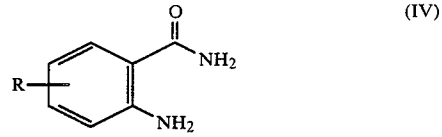

wherein R is as define above.
2. The process according to claim 1, in which R is hydrogen.
3. The process according to claim 1, in which the reaction is carried out at a temperature between 50° and 150° C.
4. The process according to claim 3, in which the reaction is carried out at a temperature between 80° and 100° C.
5. The process according to claim 1, in which said solvent is N,N-dimethyl-formamide.

* * * * *